(12) United States Patent
Urano et al.

(10) Patent No.: US 8,908,172 B2
(45) Date of Patent: Dec. 9, 2014

(54) DEFECT INSPECTION DEVICE AND METHOD OF INSPECTING DEFECT

(75) Inventors: Takahiro Urano, Ebina (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 36 days.

(21) Appl. No.: 13/575,050

(22) PCT Filed: Feb. 9, 2011

(86) PCT No.: PCT/JP2011/000705
§ 371 (c)(1),
(2), (4) Date: Jul. 25, 2012

(87) PCT Pub. No.: WO2011/105016
PCT Pub. Date: Sep. 1, 2011

(65) Prior Publication Data
US 2012/0293795 A1    Nov. 22, 2012

(30) Foreign Application Priority Data
Feb. 26, 2010  (JP) ................................ 2010-041272

(51) Int. Cl.
    *G01N 21/00*  (2006.01)
    *G01N 21/95*  (2006.01)
(52) U.S. Cl.
    CPC .................................. *G01N 21/9501* (2013.01)
    USPC ...................................................... 356/237.5
(58) Field of Classification Search
    USPC ...................................................... 356/237.5
    See application file for complete search history.

(56) References Cited

U.S. PATENT DOCUMENTS

| 5,903,342 A | 5/1999 | Yatsugake et al. |
| 2005/0185172 A1 | 8/2005 | Ishimaru et al. |
| 2008/0304055 A1* | 12/2008 | Oshima et al. ............. 356/237.5 |
| 2009/0244529 A1 | 10/2009 | Oka et al. |
| 2009/0290168 A1 | 11/2009 | Hamamatsu et al. |

FOREIGN PATENT DOCUMENTS

| JP | 9-304289 | 11/1997 |
| JP | 2006-201179 | 8/2006 |
| JP | 2008-32600 | 2/2008 |
| JP | 2008-58239 | 3/2008 |
| JP | 2010-2406 | 1/2010 |

* cited by examiner

*Primary Examiner* — Tarifur Chowdhury
*Assistant Examiner* — Jamil Ahmed
(74) *Attorney, Agent, or Firm* — Antonelli, Terry, Stout & Kraus, LLP.

(57) ABSTRACT

Disclosed is a defect inspection device comprising: an illumination optical portion which illuminates an object to be inspected with illuminating light; a detection optical portion system illuminated by the illumination optical portion and provided with a plurality of detectors which respectively detects components of scattering light which scatter from the inspected object each in a different direction of azimuthal angle or in a different direction of angle of elevation with respect to a surface of the inspected object; and a signal processing portion which makes gain adjustments and defect decisions in parallel on plural signals based on the components of the scattering light from the inspected object detected by the detectors, respectively, the defect decisions being based on a threshold value decision, and which extracts defects based on results of the gain adjustments and of the defect decisions.

12 Claims, 17 Drawing Sheets

FIG. 4(a)
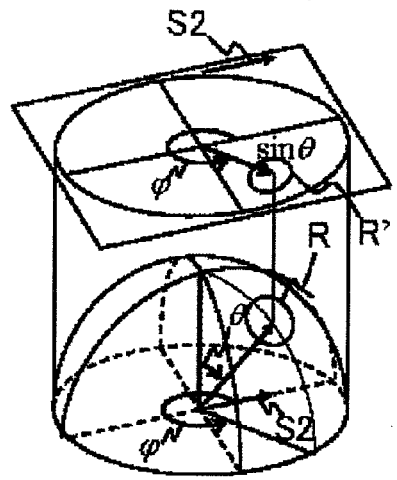
FIG. 4(b-1)
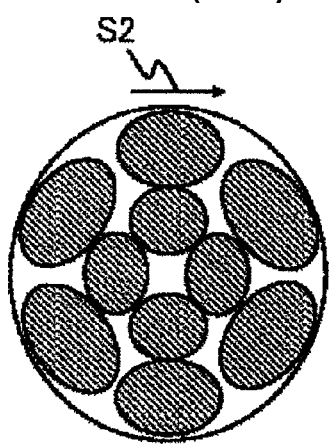
FIG. 4(b-2)
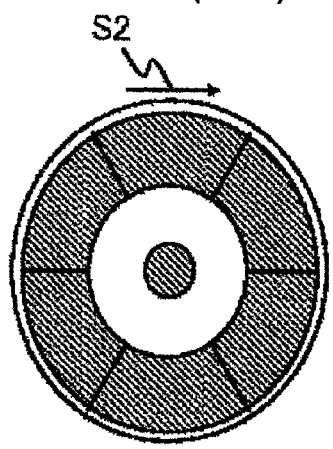

FIG. 4(c-1)
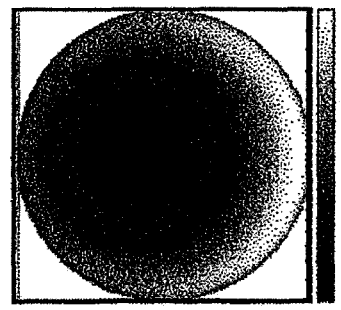
DEFECT SPECIES A
FIG. 4(c-2)
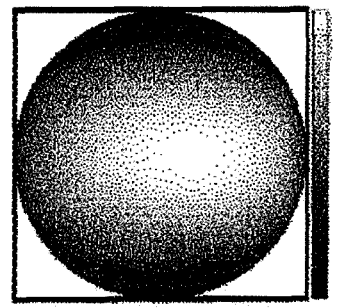
DEFECT SPECIES B
FIG. 4(c-3)
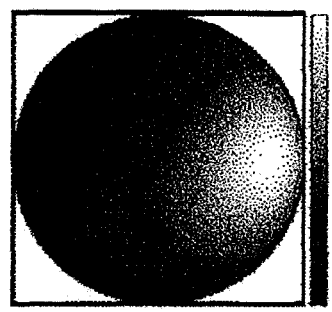
DEFECT SPECIES C FIG. 7(a)
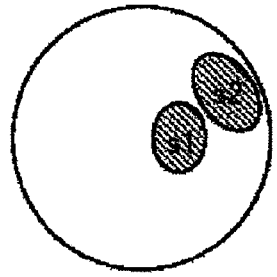
FIG. 7(b-1)
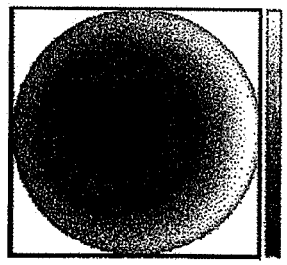
DEFECT SPECIES A
FIG. 7(b-2)
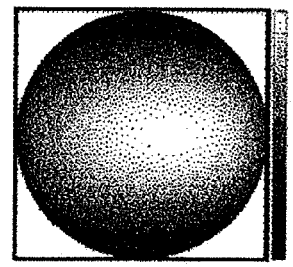
DEFECT SPECIES B

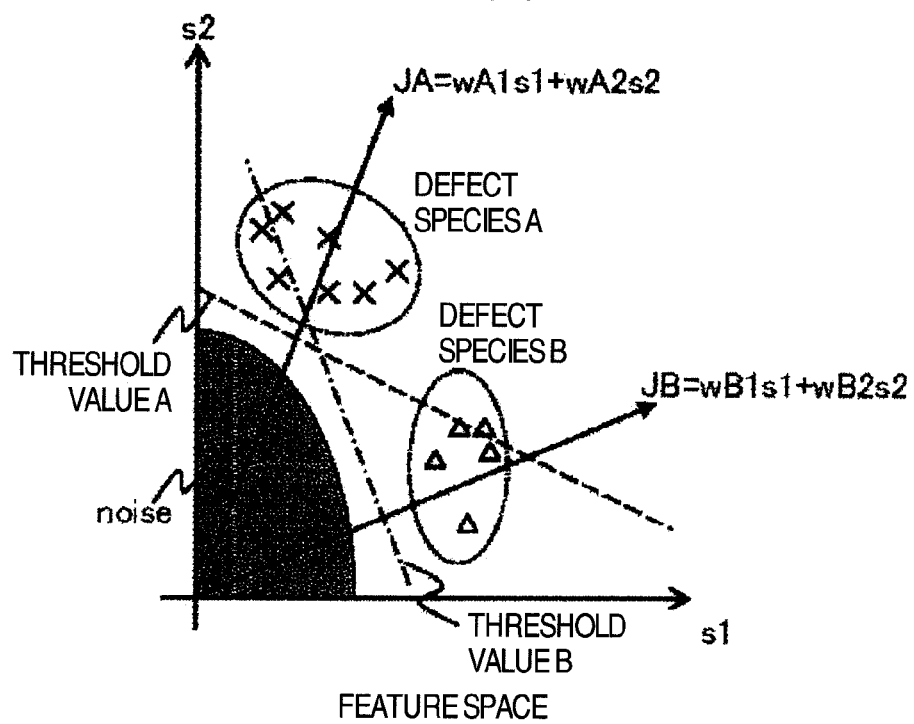

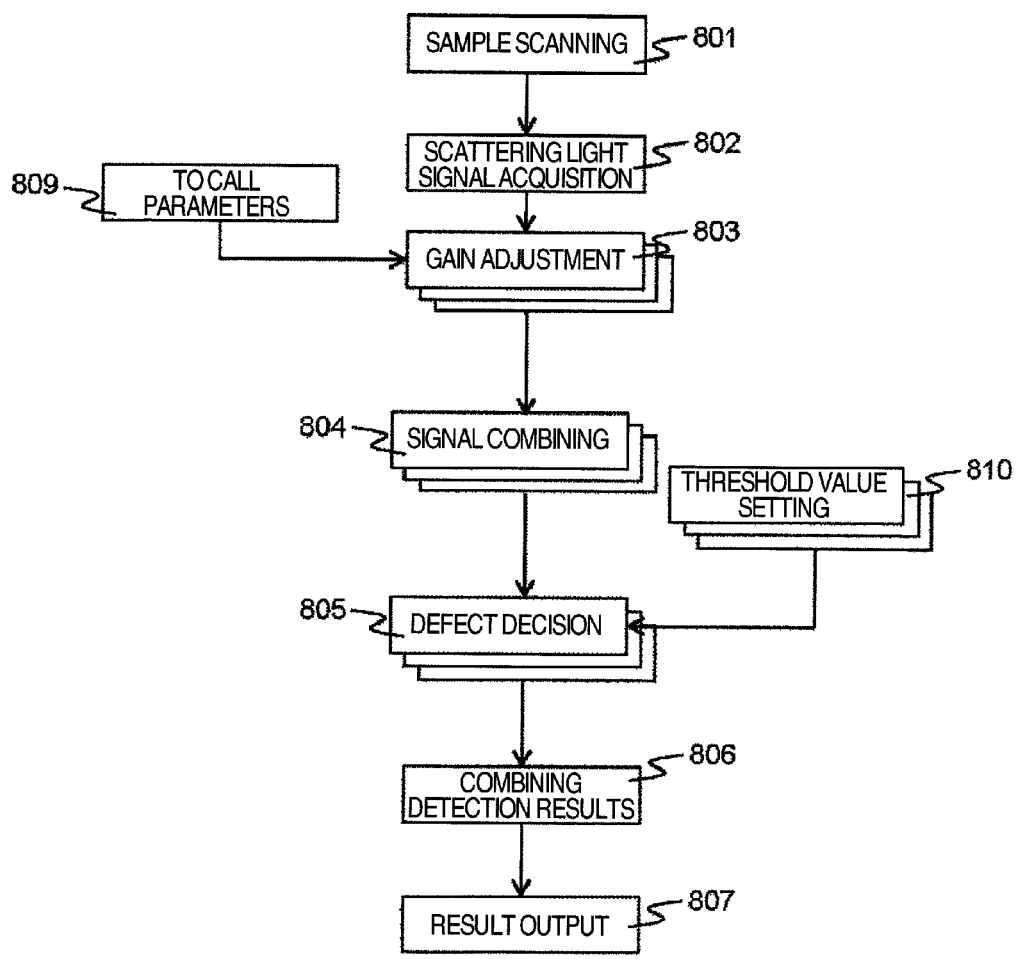

FIG. 11

DEFECT INSPECTION DEVICE AND METHOD OF INSPECTING DEFECT

TECHNICAL FIELD

The present invention relates to a defect inspection device and defect inspection method for inspecting microscopic defects present on or in the surface of a sample at high sensitivity.

BACKGROUND ART

On a manufacturing line for semiconductor substrates, thin-film substrates, and so on, defects present on or in the surfaces of the semiconductor substrates, thin-film substrates, and so on are inspected to maintain or improve the product yield.

As a conventional technique, an inspection device or tool for inspecting defects having dimensions from tens of nm to the order of microns or more by directing a laser beam collected to tens of microns at the surface of a sample for detecting microscopic defects and collecting and detecting scattering light from the defects is disclosed in patent literature 1 (JP-A-9-304289). An inspection tool for classifying defects by detecting those components of scattering light from the defects which exit at high angles and those components which exit at low angles and relying on their ratio is disclosed in patent literature 2 (JP-A-2006-201179).

Furthermore, patent literature 3 (JP-A-2008-32600) discloses an "outer appearance inspection tool having a signal combining portion for combining detection signals based on scattering light generated from a surface of a sample according to set conditions, a condition setting portion for setting conditions under which the detection signals are combined together by the signal combining portion, and a display portion for displaying a synthesized sample image built based on the resulting signal created by the signal combining portion according to the conditions set by the condition setting portion".

CITATION LIST

Patent Literature

Patent Literature 1: JP-A-9-304289
Patent Literature 2: JP-A-2006-201179
Patent Literature 3: JP-A-2008-32600

SUMMARY OF INVENTION

Technical Problem

As circuit patterns get finer, defects to be detected even in mirror wafers prior to formation of circuit patterns become finer. It is desired that defects of various shapes be detected at high sensitivity. In the past, in order to capture a wide distribution of scattering light components of different characteristics due to differences in defect shape and size, plural detectors present at different angles and positions have been disposed. Detection signals have been combined into one under arbitrary conditions. Its signal intensity has been processed using a threshold value, thus detecting defects.

However, where one attempts to detect defects of various shapes at high sensitivity, it is difficult to detect plural defect species at the same time under a single combination condition as disclosed in patent literature 3. On the other hand, by treating signals obtained from detectors as multidimensional feature quantities without combining together the signals, it is possible to detect plural detects. However, there arises the problem that computational cost associated with signal processing such as computation of boundary threshold values for discrimination between defects and noises on a sample is increased with increasing detectors.

Solution to Problem

Summaries of typical ones of inventions disclosed in the present application are briefly described as follows.

(1) A defect inspection device having an illumination optical portion for illuminating an object to be inspected with illuminating light, a detecting optical portion illuminated by the illumination optical portion and equipped with plural detectors operating to detect components of scattering light scattering from the inspected object each in a different direction of azimuthal angle or in a different direction of angle of elevation with respect to a surface of the inspected object, and a signal processing portion for making defect decisions as to plural signals based on the scattering light components from the inspected object detected by the detectors, respectively, such that the defect decisions are performed in parallel based on gain adjustments and threshold value decisions and for extracting defects based on results of the gain adjustments and defect decisions.

Advantagenous Effects of Invention

According to the present invention, it is possible to offer a defect inspection device and defect inspection method that inspects microscopic defects present on or in the surface of a sample at high sensitivity.

BRIEF DESCRIPTION OF DRAWINGS

FIG. 4(a) is a schematic view showing the arrangement of the detection portion of the embodiment of the defect inspection device associated with the invention.

FIG. 4(b-1) is a schematic view showing the arrangement of the detection portion of the embodiment of the defect inspection device associated with the invention.

FIG. 4(b-2) is a schematic view showing the arrangement of the detection portion of the embodiment of the defect inspection device associated with the invention.

FIG. 4(c-1) is a scattering light distribution of a defect species A.

FIG. 4(c-2) is a scattering light distribution of a defect species B.

FIG. 4(c-3) is a scattering light distribution of a defect species C.

FIG. 7(*a*) is an arrangement plan view of a low-angle detector and a high-angle detector.

FIG. 7(*b*-1) is a scattering light distribution of a defect species A.

FIG. 7(*b*-2) is a scattering light distribution of a defect species B.

FIG. 7(*c*) is an explanatory view of a feature space in a signal combining portion of an embodiment of a defect inspection device associated with the present invention.

FIG. 8 is a block diagram illustrating the flow of defect-detecting processing of a defect inspection device associated with the present invention.

FIG. 11 is an explanatory view of a method of displaying a simulator for setting of gain adjustment parameters.

DESCRIPTION OF EMBODIMENTS

Embodiment 1

Figure 1:
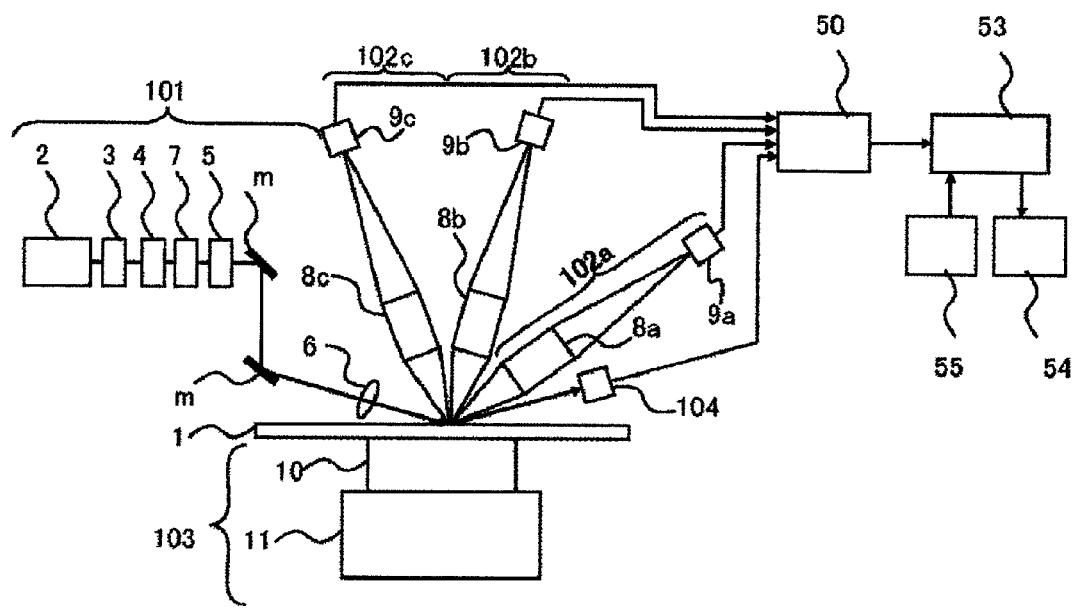
FIG. 1 is a block diagram of an embodiment of a defect inspection device associated with the present invention.

One example of an embodiment of a defect inspection device or tool associated with the present invention is described with reference to FIG. 1. The defect inspection device set forth in FIG. 1 is configured including an illumination portion 101, a detection portion 102 (102*a*, 102*b*, 102*c*), a stage 103 on which a sample 1 can be placed, a signal processing portion 50, an overall control portion 53, a display portion 54, and an input portion 55. A regular reflection detection portion 104 is installed as necessary for a purpose such as large-area defect inspection or measurement of a sample surface.

The illumination portion 101 is configured including a laser light source 2, an attenuator 3, a polarizing element 4, a beam expander 7, an illuminance distribution control device 5, a reflecting mirror m, and a condenser lens 6. Laser light emitted from the laser light source 2 is adjusted to a desired beam strength by the attenuator 3, adjusted to a desired state of polarization by the polarizing element 4, adjusted to a desired beam diameter by the beam expander 7, and made to illuminate an inspected region of the sample 1 via the reflecting mirror m and condenser lens 6. The illuminance distribution control device 5 is used to control the illumination intensity distribution on the sample 1. In FIG. 1, a configuration in which light is obliquely directed at an angle to the line normal to the sample 1 by the illumination portion 101 is shown. A separate illumination optical path (not shown in FIG. 1) which makes it possible to illuminate the surface of the sample 1 perpendicularly to the surface may also be had. The illumination optical path can be switched.

A laser light source which emits ultrashort wavelength UV or vacuum ultraviolet laser beam as a wavelength not easily penetrating into the sample and which produces a high output of 1 W or more is used as the laser light source 2 to detect very small or microscopic defects near the surface of the sample. In order to detect defects inside the sample, one which emits a visible or infrared laser beam as a wavelength easily penetrating into the sample is used.

The stage 103 is configured including a translational motion stage 11, a rotary stage 10, a z-motion stage (not shown).

Figure 2:
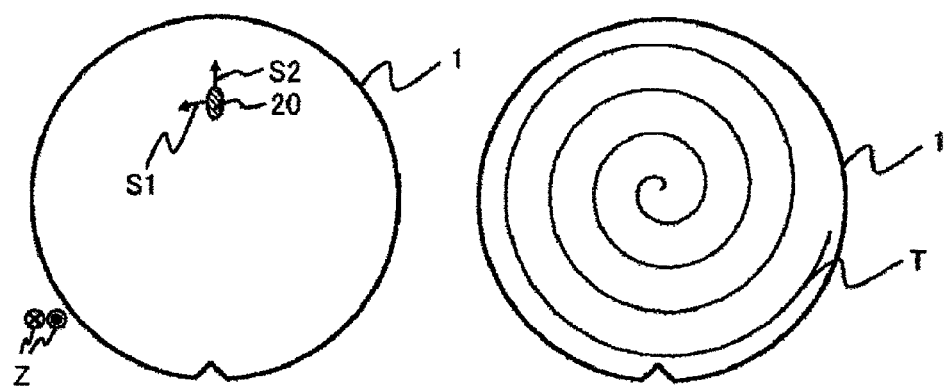
FIG. 2 is a schematic view showing a method of scanning a sample.

FIG. 2 is a schematic view showing a method of scanning a sample, showing the relation between an illuminated region (illumination spot 20) on the sample 1 and the direction of scanning owing to motions of the rotary stage 10 and of the translational motion stage 11 and the trajectory of the illuminated field 20 drawn thereby on the sample 1. In FIG. 2, the shape of the illuminated field (linear illumination) 20 formed in the form of an elliptical shape (linear) that is long in one direction and short in the direction perpendicular to it by the illuminance distribution control in the illumination portion 101 or by oblique illumination is shown. The illuminated field 20 is scanned in the circumferential direction Si of a circle centered at the axis of rotation of the rotary stage 10 by the rotational motion of the rotary stage 10 and in the direction of translational motion S2 of the translational motion stage 11 by its translational motion. The illumination portion 101 is so configured that the longitudinal direction of the illumination spot 20 is parallel to the scanning direction S2 and that the illumination spot 20 passes across the axis of rotation of the rotary stage 10 by the scanning in the scanning direction S2. Motion of the Z stage corresponds to the height of the sample 1, i.e., movement in the normal direction to the surface of the sample 1.

In the configuration described so far, the illumination spot is made to draw a spiral trajectory T and to scan the whole surface of the sample 1 by making a scan in the scanning direction S2 over a distance equal to or less than the length of the illumination spot 20 in the longitudinal direction while the sample is being rotated once by scanning in the scanning direction S1.

The detection portions 102*a*, 102*b*, and 102*c* of FIG. 1 are configured to collect and detect components of scattering light produced at respectively different azimuthal angles and angles (elevation angles) with respect to the surface of the sample.

FIGS. 3(*a*)-3(*d*) are block diagrams showing one example of the detection portions of an embodiment of a defect inspection device associated with the present invention. A specific configuration of the detection portion 102*a* shown in FIG. 1 is shown.

Since constituent elements of the detection portions 102*b* and 102*c* are common to those of the detection portion 102*a*, their description is omitted. In a manner not set forth in FIG. 1, a plurality of detection portions which are different in direction of detection relative to the surface of the sample may be arranged besides the detection portions 102*a*, 102*b*, and 102*c* to detect scattering light in a wide angular range as described later in connection with FIG. 4.

Figure 3A:
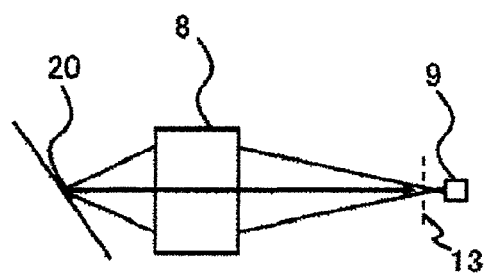
FIG. 3(a) is a block diagram showing one example of detection portion of an embodiment of a defect inspection device associated with the present invention.

The detection portion 102a shown in FIG. 3(a) is configured including an optical collection system 8, a polarizing filter 13, and a sensor 9. Because of the optical collection system 8, an image of the illumination spot 20 is focused onto the photosensitive surface of the sensor 9 or its vicinity. Background light produced from the positions other than the illumination spot can be removed or reduced by installing a field aperture (not shown) of an appropriate diameter in the focal position. The polarizing filter 13 can be brought into and out of the optical axis of the imaging system (optical collection system) 8 and can rotate in the azimuth of light detection, and is used for the purpose of reducing scattering light components due to roughness or the like of the sample becoming a factor resulting in noises.

A wire grid polarization plate exhibiting high transmissivities and extinction ratios at short wavelengths such as ultraviolet rays or a polarization beam splitter is used as the polarizing filter 13. A thin film of a metal such as aluminum or silver is microfabricated on fringes is available as the wire grid polarization plate.

To permit detection of feeble scattering light from foreign materials, a semiconductor optical detector coupled with a photomultiplier, an avalanche photodiode, an image intensifier, or the like is used as the sensor 9. Preferably, an ultrabialkali or super-bialkali type having a high quantization efficiency is used as the photomultiplier for realizing high sensitivity and high accuracy.

Figure 3B:
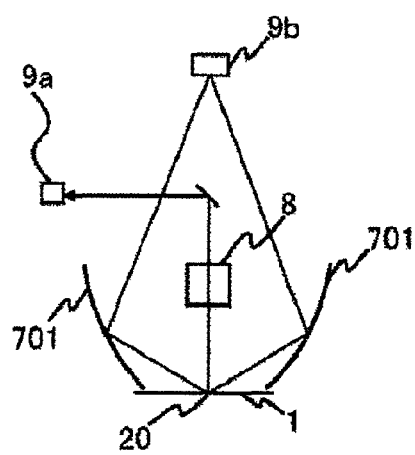
FIG. 3(b) is a block diagram showing a modified example of the detection portion of the embodiment of the defect inspection device associated with the invention.

An example in which the optical collection system is configured by a reflective optical system owing to an ellipsoidal mirror is shown in FIG. 3(b). The optical collection system 701 is so arranged that a first focal position of an ellipse is taken as a position hit by illuminating light and that the position of a second focal position is disposed at the photosensitive surface of a sensor 9b. The optical collection system 701 is adapted to collect scattering light at high NA including shallow angles relative to the wafer surface and to guide the light to the sensors. In addition, the optical collection system has a detection portion having the optical collection system 8 and a sensor 9a and operating to detect upwardly scattering light, and is so configured to be capable of detecting components of scattering light in plural directions simultaneously.

Figure 3C:
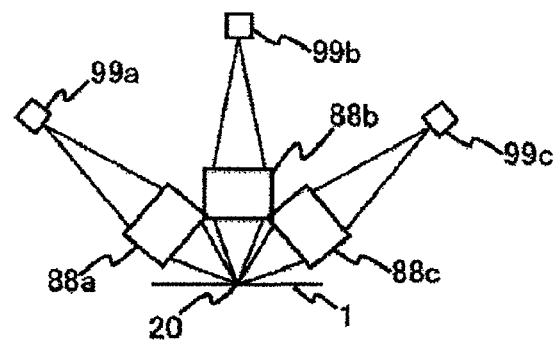
FIG. 3(c) is a block diagram showing a modified example of the detection portion of the embodiment of the defect inspection device associated with the invention.

FIG. 3(c) is an example of configuration of the detection portion that collects scattering light from plural directions and images the light onto an image sensor. The detection portion is so configured that scattering light components in plural directions which are different in azimuth or elevation angle are imaged onto image sensors 99a, 99b, and 99c by optical collecting and imaging systems 88a, 88b, and 88c. Defects produced on or in a circuit pattern such as a semiconductor wafer, mask, or the like having the circuit pattern thereon can be detected by detecting scattering light from the sample surface as an image and performing image processing. Therefore, this is effective in inspecting a sample on which a pattern has been formed.

A linear array sensor or a two-dimensional array sensor composed of CCDs or CMOSes, a high-sensitivity image sensor consisting of an image intensifier coupled to such a sensor, or a multianode photomultiplier tube is used as the image sensor.

Figure 3D:
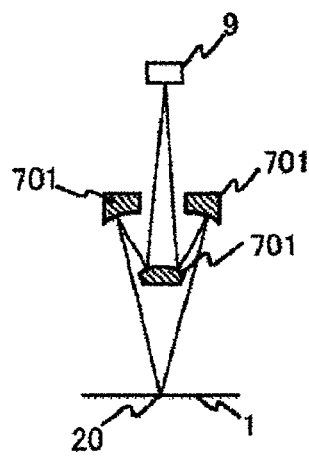
FIG. 3(d) is a block diagram showing a modified example of the detection portion of the embodiment of the defect inspection device associated with the invention.

FIG. 3(d) is an example of configuration using a reflective optical system relying on Schwartzschild optics. This is adapted to image scattering light onto the sensor 9 in a case where illumination is made at a short wavelength equal to or less than 200 nm.

Then, the relations between the angular components of scattering light detected by the detection portions 102a, 102b, and 102c are shown by referring to FIGS. 4(a), 4(b-1), and 4(b-2).

FIG. 4(a) is a schematic view showing the arrangement of detection portions of an embodiment of a defect inspection device associated with the present invention. FIG. 4(a) shows a hemisphere whose equatorial plane corresponds to the surface of a sample and whose zenith is in the direction normal to the sample surface. Let φ be an azimuthal angle (longitude) relative to the scanning direction S2. Let θ be an angle from the zenith. An angular range detected by the detection portions 102a, 102b, etc. are indicated by a range R on the hemisphere. This is parallel projected onto the surface parallel to the equatorial plane. The results are shown as FIGS. 4(b-1) and 4(b-2).

In FIGS. 4(b-1) and 4(b-2), the range of angles detected by the detection portions 102a, 102b, etc. is shown by shaded oblique lines. As shown in FIGS. 4(b-1) and 4(b-2), various kinds of defect species can be detected by providing plural detection portions so as to cover a wide range of angles. The distribution of angles of defect scattering light differs according to defect species and defect dimensions and so the defect species and defect dimensions can be classified and estimated accurately by detecting the intensities of scattering light at various angles by the plural detection systems at the same time and performing processing by a signal processing portion described later.

FIG. 4(b-1) is one example of the arrangement of a detection system adapted to inspect foreign materials ranging from quite small dimensions to large dimensions. Where P polarization illumination is made, scattering light off quite small foreign materials appears strongly at low angles of elevation direction relative to the surface of the sample. Quite small defects can be detected by detecting low-angle scattering light components over the whole range of azimuths. Furthermore, cratering or concave defects such as crystal originated particles (COPs) which show strong scattering light at high angles can be detected at high sensitivity by detecting scattering light components appearing at high elevation angles. In addition, it is possible to grasp the feature of a scattering light distribution that differs according to defect by arranging plural detectors in each of θ direction and φ direction.

FIG. 4(b-2) is an example in which a detection portion for making detections over the whole azimuthal range at low angle elevation directions relative to the surface of a sample and a detection portion for detecting scattering light in the direction normal to the sample are installed. Scattering light in all the azimuths in a certain range of θ angles can be collected by using an ellipsoidal mirror whose one focus is in the illumination spot position as shown in FIG. 3(b) as the optical collection system 8. Furthermore, scattering light components in plural azimuths can be detected at once by installing a spatial filtering unit or an optical path branching unit in the optical collection system optical path and installing their respective detectors. In either configuration, scattering light which is produced in different directions according to defect can be detected and various defects can be detected robustly by picking up scattering light in a wide angular range.

In FIGS. 4(c-1)-4(c-3), examples of continuous scattering light distribution of defects corresponding to plural illumination conditions are shown by the angle representation method shown in FIG. 4(a). FIGS. 4(c-1)-4(c-3) show the scattering light distributions of defect species A, B, and C, respectively. These indicate that the different defect species produce different scattering light distributions and that as color becomes denser, the scattering intensity weakens.

The configuration of the defect decision portion 50 of an embodiment of a defect inspection device associated with the present invention is next described.

Figure 5:
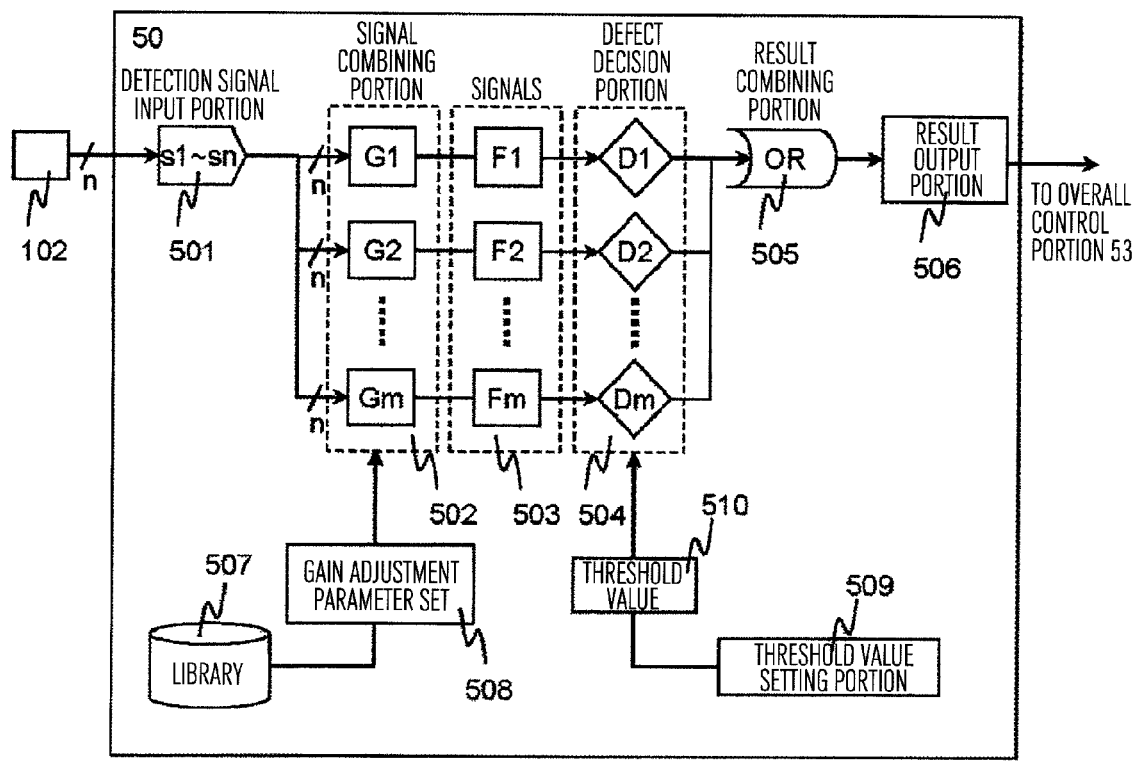
FIG. 5 is a block diagram of a signal processing portion of an embodiment of a defect inspection device associated with the present invention.

FIG. 5 is a block diagram of the signal processing portion of the embodiment of the defect inspection device associated with the present invention. The signal processing portion has a detection signal input portion 501 for entering detection signals s1-sn obtained from the detectors 102, a signal combining portion 502 including at least one signal combining unit or units G1-Gm, a defect decision portion 504 including defect decision units D1-Dm to which signals 503 (F1-Fm) delivered from the signal combining units G1-Gm are applied, a result combining portion 505 for combining defects detected by the defect decision portion 504, and a defect output portion (defect output portion) 506 outputting the results obtained by the combining done by the result combining portion 505 to the overall control portion 53.

The signal combining units G1-Gm operate to make gain adjustments based on an arbitrary gain value for the input signals s1-sn which have been detected by gathering scattering light components produced at different azimuthal angles and elevation angles (angles) relative to the surface of a sample and to output combined signals F1-Fm. The gains for the signal combining units G1-Gm are adjusted using a set of gain adjusting parameters 508 having different gain adjustment ratios. The parameters of the set of gain adjusting parameters 508 are set by a library 507. Preferably, combinations of signals owing to the signal combining units G1-Gm are parallel processed. By parallel processing signal combinations for the detection signals s1-sn, the processing time can be prevented from increasing, and a high throughput can be accomplished.

In the present invention, any type of defect species can be detected at high sensitivity by combining together signals by the use of the signal combining units G1-Gm having different detection characteristics for signals detected from defects such as foreign materials and scratches which differ in scattering light characteristics.

It is assumed, for example, that the signal combining unit G1 is sensitive to signals in the directions of low angles of elevation relative to the surface of a sample and that the signal combining unit G2 is sensitive to signals at high angles. Where input signals from the defect species A described in FIG. 4(*c*-1) are combined together by the signal combining unit G1, high sensitivity detection is achieved but high sensitivity detection is impossible to achieve by the signal combining unit G2. On the other hand, the defect species B of FIG. 4(*c*-2) can be inspected at high sensitivity by the signal combining unit G2. In this way, by providing plural signal combining units having different detection characteristics, plural defect species can be detected all at high sensitivity.

However, it is difficult to previously know what type of defect species is present on the sample. Therefore, in the present invention, the signal combining units G1-Gm are made to process at the same time in parallel. Consequently, a defect decision coping with all types of defect species is accomplished.

In response to the output signals 503 (F1-Fm) from the signal combining portion 502, the defect decision portion 504 performs a defect decision by threshold value processing. The decision portion outputs a two-valued result indicating whether or not it is a defect. The result combining portion 505 combines together the two-valued results delivered from the plural defect decision units D1-Dm equipped in the defect decision portion 504, thus making a decision as to whether or not the defect signal is a defect. By using a logical sum for any combination of detection results, if a defect is detected from a signal obtained by combining done by at least one signal combining unit, then it is possible to judge that there is a defect. Omission of defects can be prevented.

Furthermore, as shown in FIG. 5, higher sensitivity can be accomplished without lowering the throughput by causing defect detection processing operations in the units such as the signal combining units G1-Gm and defect decision units D1-Dm to be carried out in parallel.

The input signals s1-sn described herein are taken as detection signal intensities obtained from detectors which are different in azimuth or angle of elevation. Instead of signal intensities, feature quantities extracted from input signal intensities may be treated as input signals. Since the input signals include variations across various positions on the sample and variations among detectors, normalization or whitening may be carried out in a stage prior to inputting. If normalization or whitening is performed, noise components of detection signals are reduced, and more accurate defect inspection can be accomplished.

Figure 6:
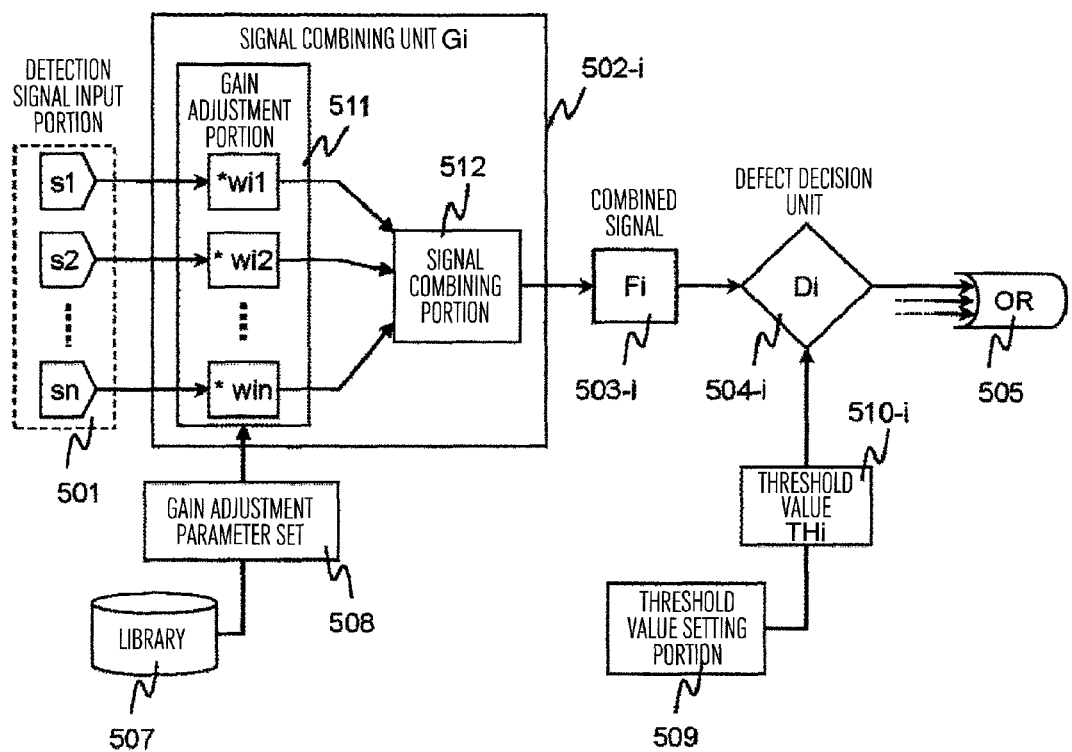
FIG. 6 is a block diagram showing details of a signal combining portion and a defect decision portion of an embodiment of a defect inspection device associated with the present invention.

FIG. 6 is a block diagram showing details of the signal combining portions 502 and defect decision portions (defect discrimination portion) 504 of an embodiment of a defect inspection device associated with the present invention. Here, a description is made while taking notice of one signal combining unit Gi (502-*i*) and one defect decision unit Di (504-*i*).

The signal combining unit Gi is configured including a gain adjustment portion 511 for adjusting gains for input signals from the signal input portions s1-sn (501) by means of parameters wi1-win and a signal combining portion 512 for combining the gain-adjusted signals and outputting an integrated signal Fi (503-*i*). In the gain adjustment portion 511, the gain adjustment parameters wi1-win may refer to the set of gain adjustment parameters 508 previously stored in the library 507. The signal combining portion 512 combines the gain-adjusted signals into a one-dimensional scalar amount with some function Ji (s) and outputs a combined signal Fi=Ji (s). This combined function Ji may be a linear combined function as given by the following equation.

$$Ji(s)=wi1*s1+wi2*s2+ \ldots +win*sn$$

In the gain adjustment portion 511, gain adjustments are made on the input signals s1-sn. In the case of a scattering light distribution giving high values of signal from detectors for low angles of elevation like the defect species A in FIG. 4(*c*-1), if one wants to detect the defect species A at high sensitivity, the gain adjustment parameters should be set as follows, where sL is an input signal from the detector located at a low angle of elevation and sH is an input signal from the detector located at a high angle of elevation.

$$J(s)=wL*sL+wH*sH \text{ (where } wL>wH)$$

Furthermore, where there is an isotropic scattering light distribution at each angle of elevation for detection as encountered in the case of granular foreign materials, defects can be detected at high sensitivity by setting gain adjustment parameters for the detection signal at each angle of elevation such that sL1=sL2= . . . sLn.

In addition, where other concave defects or the like are inspected, the defects can be detected at high sensitivity by setting gain adjustment parameters based on scattering light characteristics.

In this way, by performing integration into a one-dimensional signal in response to multidimensional data that are a plurality of input signals s1-sn, defect decision can be realized while the defect decision portion needs to perform only simple threshold value processing. Consequently, processing can be carried out at high speed.

Then, the defect decision unit Di (504-$i$) makes defect decisions using the combined signal Fi (503-$i$) delivered from the signal combining unit Gi and the threshold value THi (510-$i$) delivered from a threshold value setting portion 509, and outputs a two-valued output signal indicating whether or not the detected object is a defect to the result combining portion 505.

The combined signals Fi inputted to the defect decision unit Di are combined together by a coupling function that is different for each signal combining unit Gi and so noise and defect signal intensities are not constant. Therefore, it is necessary to carry out decision processing relying on a threshold value that differs according to each defect decision unit Di. In the threshold value setting portion 508, as a method of setting each individual threshold value for each unit, the threshold value can be set based on fixed threshold values for individual units and on noise intensity estimated from a HAZE intensity detected in the regular reflection detection portion 104.

Further, a value specified by the user may be used. Where a normalized signal is used as an input to the signal combining unit, a constant threshold value can be set for each unit.

FIGS. 7($a$)-($c$) are views showing one example of signal combination. FIG. 7($a$) is a layout diagram of detectors for high and low angles. FIGS. 7($b$-1) and ($b$-2) are scattering light distributions of defect species A and B. FIG. 7($c$) is an explanatory view of a feature space in a signal combination portion of an embodiment of a defect inspection device associated with the present invention.

As shown in FIG. 7($a$), it is assumed that s1 and s2 are detection signals which are input signals from detectors for high angles of elevation and low angles of elevation and that they are two-dimensional (two detectors) inputs. Furthermore, it is assumed that detected defects are defect species A of FIG. 7($b$-1) producing low angles s2 of scattering light detected strongly and defect species B of FIG. 7($b$-2) producing high angles s1 of scattering light detected strongly. The signal combining units are set to be GA for which the gain for s2 is increased and GB for which the gain for s1 is increased. In the defect decision units GA and GB, threshold values A and B are so set that noises are discriminated from defects. A signal FA obtained by combination performed by the combining function JA permits the defect species A to be detected at high sensitivity. A signal FB obtained by combination performed by the combining function JB enables the defect species B to be detected at high sensitivity.

It is possible to detect each and every one of the two defect species by finding the logic sum of the result of the defect decision in two combined signals FA and FB shown here. An example using two detectors is shown here. It can be expected that if the number of detectors is increased, defects will be inspected at higher sensitivity.

FIG. 8 is a block diagram showing the flow of processing of detection of defects, the processing being performed by a defect inspection device associated with the present invention.

The illumination portion 101, the stage 103, and so on operate to scan over the sample 1 to be inspected (801). A signal of scattering light is obtained by the plural detectors (detection portions 102) (802). The set of gain adjustment parameters 508 (gain adjustment parameters) is called up from the library 507 (809). In the signal combining portion 502, a gain adjustment is made on the scattering light signal (detection signal 501) (803). Then, the gain-adjusted signals 503 are combined together by the defect decision portion 504 (804). Then, a threshold value 510 is set by the threshold value setting portion 509 (810). The defect decision portion 504 discriminates defects from noises in response to the combined signal (805). Here, the processing operations 803-805 are performed in parallel using different gain adjustment parameters. Plural results of defect decisions are output. The obtained results of defect decisions are combined together by the result combining portion 505 (806). The result output portion 506 makes a decision as to whether or not there is a defect and provides an output indicative of the result (807).

Figure 9:
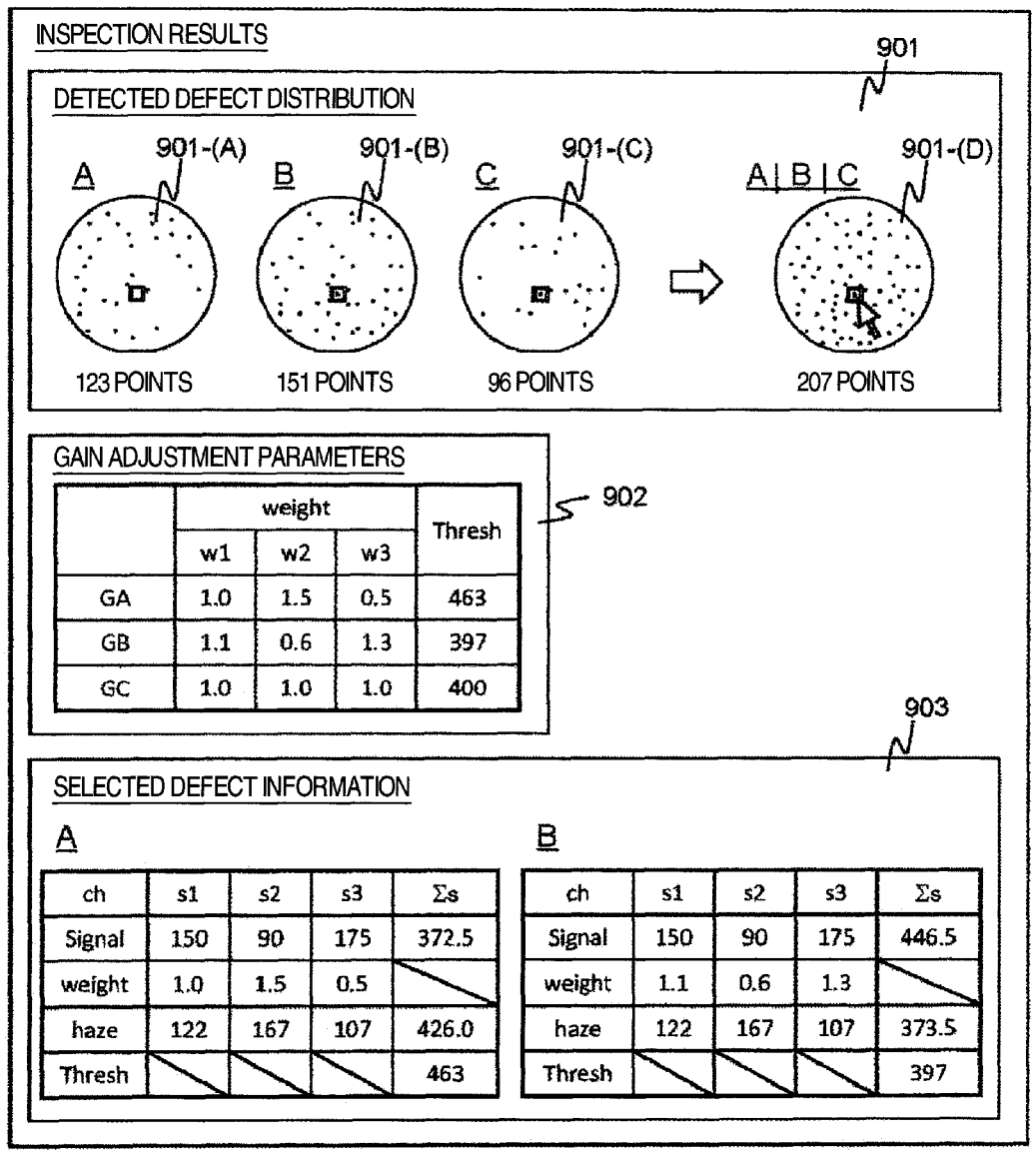
FIG. 9 is an explanatory view of a method of displaying the results of a defect detection performed by a defect inspection device associated with the present invention.

FIG. 9 is an explanatory view of a method of displaying the results of a defect detection performed by the defect inspection device associated with the present invention. FIG. 9 shows one example of GUI for outputting of the results.

Shown on the GUI screen are a detected defect distribution display portion 901 for displaying detected defect distributions 901-(A) to 901-(C) outputted from the defect decision units D1-Dm (where m=3) and a detected defect distribution 901-(D) outputted from the result combining portion, a set parameter display portion (gain adjustment parameter display portion) 902 for displaying the gain adjustment parameters set by an inspection, and a selected defect information display portion 903 showing details of defects selected from the detected defect distribution 901. On the gain adjustment parameter display portion 902, gain adjustment parameters and a threshold value which are set for each defect combining unit are displayed. If the user selects a defect that he or she wants to check from the detected defect distribution 901, then signal intensity, weight, combined signal, and so on for each signal combining unit are displayed on the selected defect information display portion 903. The user can check whether or not each unit has detected a defect. In the example of FIG. 9, it is shown that the selected defect is detected from defect decision units DB and DC but not from the defect decision unit DA.

Preparation of an LUT (look up table) that stores the gain adjustment parameters for the units is described here. Scattering light distribution characteristics of typical defect species are previously computed simulationally and optimum gain adjustment parameters are determined based on the results.

Figure 10:
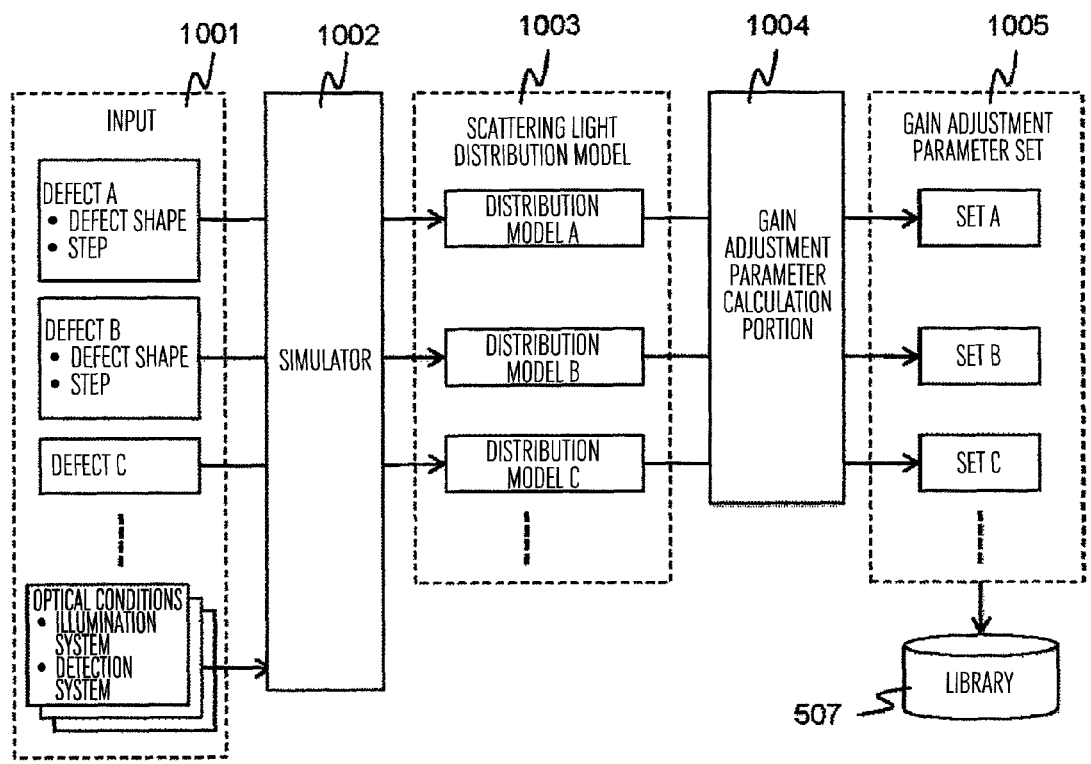
FIG. 10 is a block diagram of a gain adjustment parameter setting portion relying on a simulator.

FIG. 10 is a block diagram of a gain adjustment parameter setting portion owing to a simulator. Flow up to determination of gain adjustment parameters is described by referring to FIG. 10.

Input 1001 to the simulator, 1002, is composed of defect information to be detected and optical conditions for the inspection device. The defect information includes the shape of each defect, material, dimensions, manufacturing steps, and so on. The optical conditions include illumination conditions intrinsic to the device and detection conditions. To assume various optical conditions, plural sets of optical conditions may be entered.

The simulator 1002 finds a scattering light model 1003 for each defect species based on the input 1001 and enters it into a gain adjustment parameter calculation portion 1004. The simulation technique of the simulator 1002 is implementation of a computation program that is an FEM method, an FDTD method, a DDA method, or a BY method. Any one or plural of these techniques are loaded in the simulator. Where plural ones are loaded, an appropriate technique according to the subject of computation is selected. For example, a BV method is selected for spherical particles on a substrate. A DDA method is selected for isolated defects on or in a substrate. An FEM method or FDTD method is selected for defects of more complex shapes and pattern defects.

The gain adjustment parameter calculation portion 1004 calculates an estimated signal intensity s' detected by a detection system for each azimuth from the scattering light distribution model 1003 and then creates gain adjustment parameters wi (gain adjustment parameter set). The values of the estimated values s' of signal intensities may be directly used as the gain adjustment parameters wi. Alternatively, they may be multiplied by a certain magnification α as given by the following formula.

$$wi=\alpha*si'$$

The gain adjustment parameter calculation portion 1004 calculates a gain adjustment parameter set 1005 corresponding to all input defect species and stores the result in the library 507.

Figure 11:
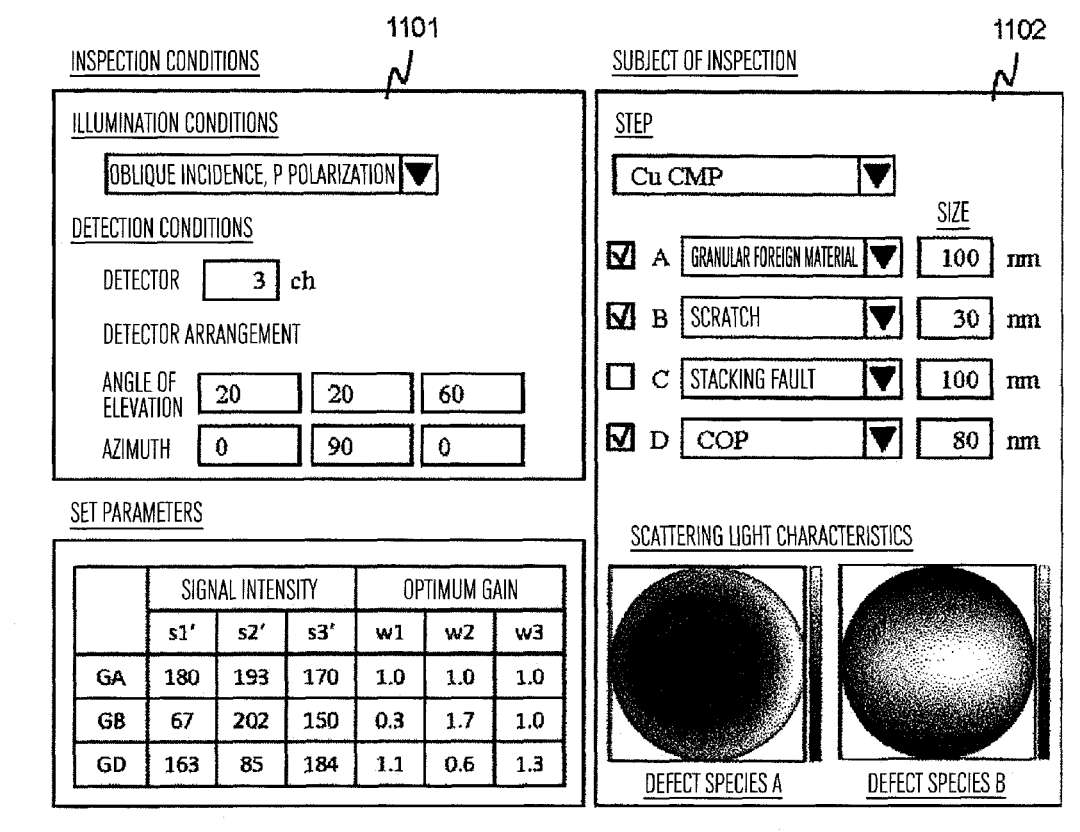

FIG. 11 is an explanatory view of a method of displaying the simulator for setting of the gain adjustment parameters. FIG. 11 is an example of GUI used for setting of the gain adjustment parameters.

The user enters inspection conditions 1101 that are optical conditions for the illumination and detection system according to the optical conditions for the device. Furthermore, the user can select and enter a processing step of interest as a subject of inspection from among a range of choices of steps held in the device. The steps are correlated with information (film structure, film type, and film thickness) about substrates indicated by defect data in the scattering light distribution library. It is possible to directly select and set film structure, film type, refractive index, and film thickness on sample surfaces in an unillustrated manner. If the optical conditions (inspection conditions) 1101 possessed by the device such as illumination conditions and detection conditions, inspection steps, defect species to be detected, and subject of inspection 1102 such as size are set, the estimated value of detection signal s' from each detector is found by the aforementioned simulation. Based on the results, an optimum gain adjustment parameter set is calculated and displayed.

In the above embodiment, a method of finding gain adjustment parameters registered in the library by a simulation is described. An embodiment of a method of calculating optimum gain adjustment parameters and registering the calculated parameters in the library by the post-processing system is shown here.

Figure 12:
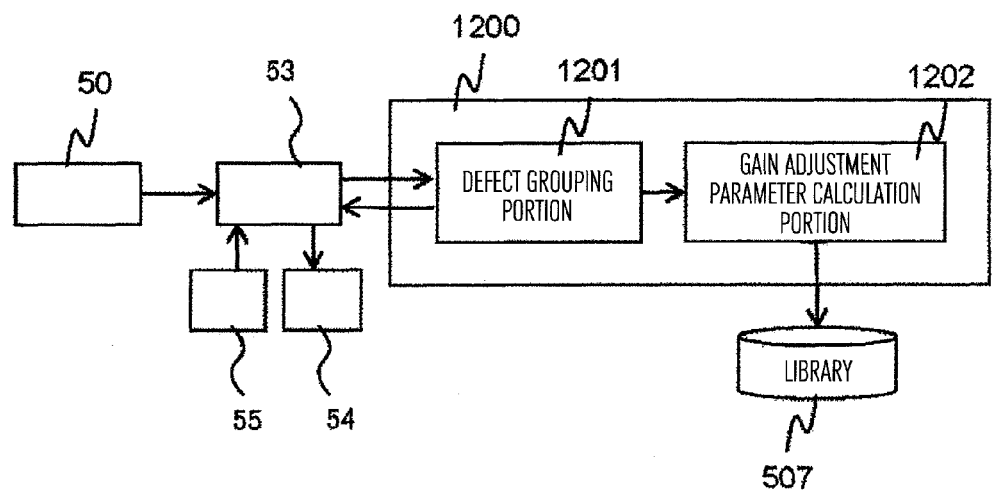
FIG. 12 is a block diagram of a post-processing system.
Figure 13:
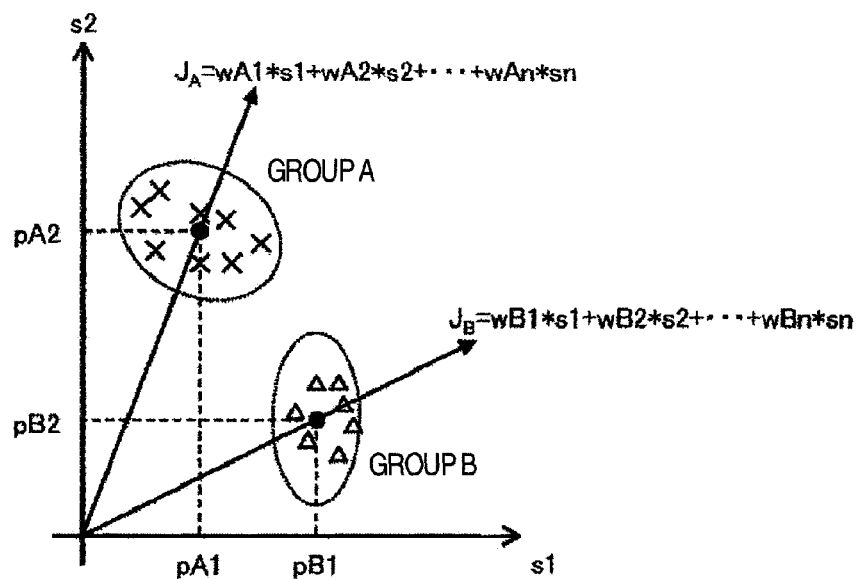
FIG. 13 is a conceptual diagram of a method of setting gain adjustment parameters.

FIG. 12 is a block diagram of the post-processing system. FIG. 13 is a conceptual view of the method of setting gain adjustment parameters.

The post-processing system, 1200, of FIG. 12 is configured including a defect grouping portion 1201 and a gain adjustment parameter calculation portion 1202.

First, the defect decision portion 50 carries out a detection of defects. Where the gain adjustment parameters are determined by the post-processing system, the inspection is performed using a low threshold value such that many defects are detected. Furthermore, the defect decision portion 50 outputs detection signals not yet combined together as well as detection results to the overall control portion 53. The post-processing system 1200 receives defect detection signals s1-sn arising from the detectors via the overall control portion 53 and groups the defect species by the defect grouping portion 1201. As one grouping method, teaching may be done based on the results of review using SEM or the like. Alternatively, clustering may be performed on the obtained defect distribution. Where teaching is performed, sampling for narrowing down defect points is necessary as a stage preceding the grouping. The gain adjustment parameter calculation portion 1202 computes the gain adjustment parameters based on the grouped defect points. As a method of calculating the gain adjustment parameters, a typical point p of each group is calculated and parameters are so set that they pass through the typical points, for example, as shown in FIG. 13. The center of gravity or median value of each group may be used as the typical point of the group.

Figure 14:
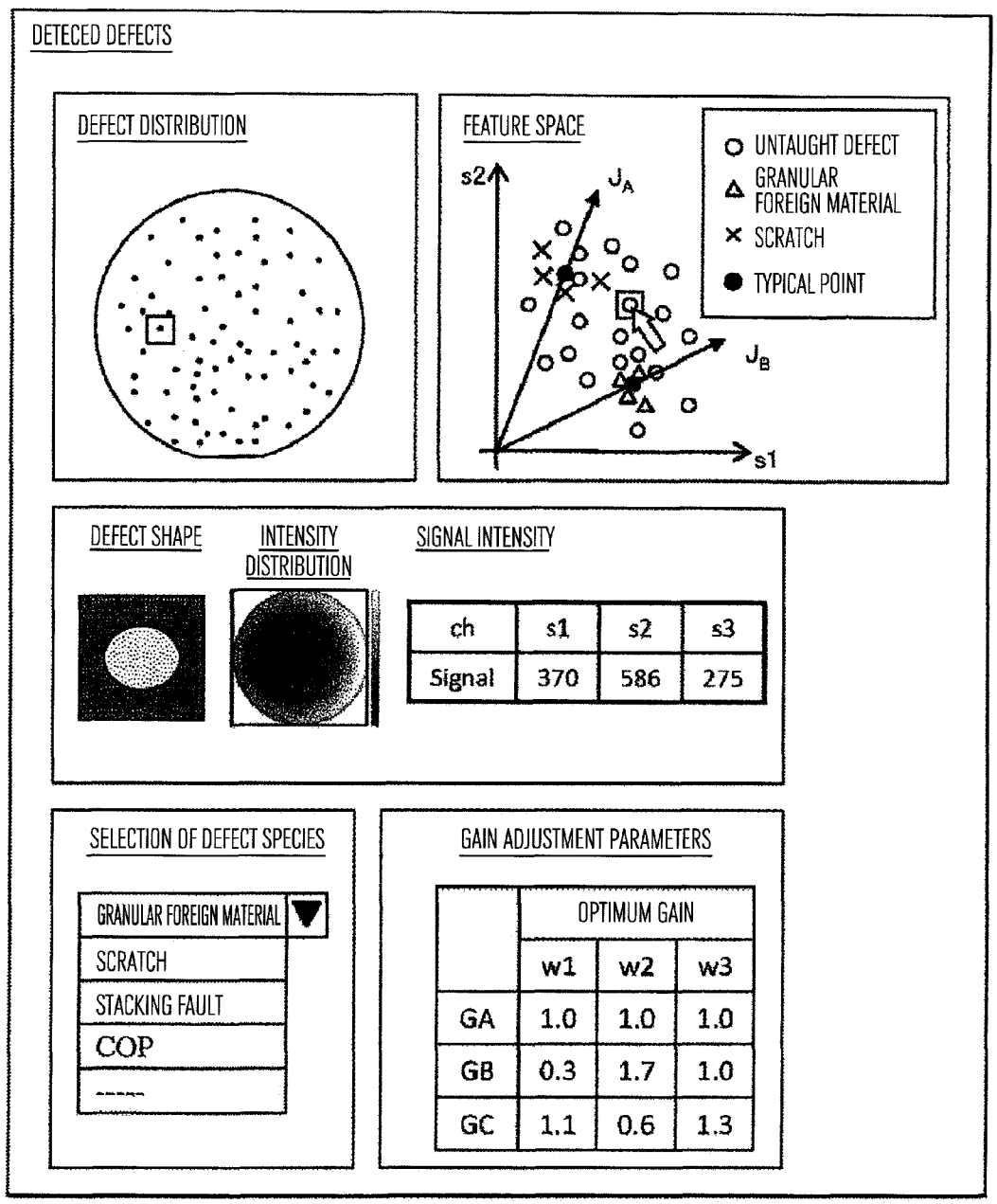
FIG. 14 is an explanatory view of a method of display provided by a post-processing system.

FIG. 14 is an explanatory view of a method of display provided by the post-processing system. FIG. 14 shows one example of GUI in a case where teaching is done for grouping.

Untaught defects are selected from the distribution of the detected defects. Defect species are selected based on defect shapes, intensity distribution, signal intensities, and so on. Gain adjustment parameters are successively calculated based on already taught defects and displayed. The gain adjustment parameters calculated by the gain adjustment parameter calculation portion 1202 set forth in FIG. 12 are stored in the library 507.

In the above embodiment, a method of finding relations between defects of known types and scattering light distribution characteristics by utilizing a simulation and calculating gain adjustment parameters from the relations is described. A method of identifying defect species from scattering light distribution characteristics in a case where detected defects are unknown is described here.

Figures 15, 16:
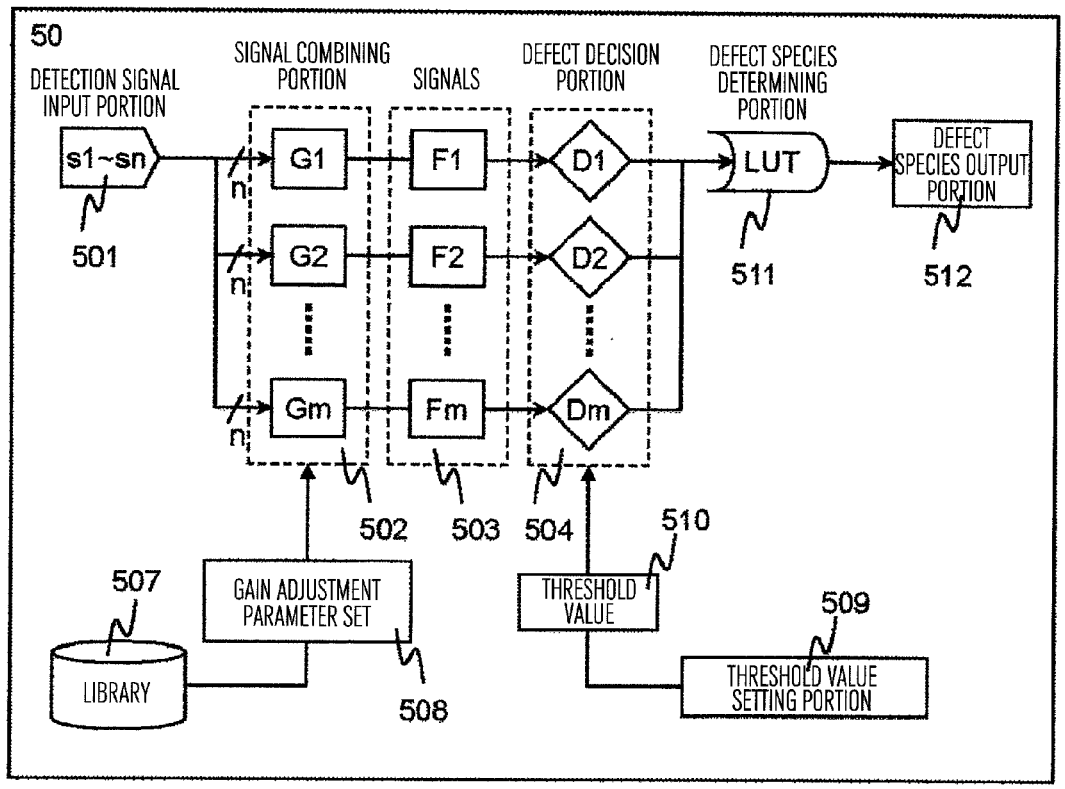
FIG. 15 is a schematic block diagram of a configuration that implements defect classification.
FIG. 16 is an explanatory view of an LUT for defect classification.

FIG. 15 is a schematic block diagram of a configuration that carries out a defect classification. FIG. 16 is an explanatory view of an LUT for a defect classification. A method of performing a classification using an LUT indicating relationships between detected defects and gain adjustment parameters is described by referring to FIGS. 15 and 16.

Defects are detected using the signal combining portion 502 and defect decision portion 504 in the same way as in the above embodiment. In the above embodiment, a logical sum is taken of defects detected from various units. Here, no logical sum is taken. Defect species are identified using an LUT 511 indicating relations between defect decision units (detection units) and defect species. One example of LUT indicating correspondence between the output from each defect decision unit and defect species is shown in FIG. 16. FIG. 16 is an LUT in which defects detected only by the defect decision unit DA are classified as defect species A and defects detected by the defect decision unit DB and DC are classified as defect species B.

As described previously, the gain adjustment parameters are so designed that defect species having certain scattering light characteristics can be detected at high sensitivity. Therefore, defects of unknown species can be classified by making use of their corresponding relationships.

In general defect classification, defect points distributed in a multidimensional feature space created by a plurality of feature quantities extracted from input signals are classified using a certain identification algorithm. In general classification algorithms, in order to determine a boundary that isolates defect species, learning relying on a multiplicity of patterns is needed. In the above embodiment, in a case where a classification algorithm is applied, it is necessary to check types and scattering light characteristics of plural defects as a learning pattern. Computational costs for the identification are also necessary. On the other hand, where defect classification is performed according to the present invention, an LUT indicating corresponding relationships with already computed gain adjustment parameters permits the defect classification to be accomplished easily and quickly.

In the above embodiment, as a method of detecting defects having different characteristics, gain adjustments are made using plural parameters which are different for detection signals, and defects are discriminated from noises on the combined signal using a hyperplane. Here, defects are discriminated from noises using an elliptic hypersphere, and a defect classification is performed based on angle.

Assuming that noise intensities show an nth-dimensional Gaussian distribution, a boundary E for discrimination between noise and defect can be represented by an nth-dimensional elliptic hypersphere. A formula for a boundary for a discrimination is given below.

$$E(s)=s1^2/T1^2+s2^2/T2^2+\ldots+sn^2/Tn^2$$

where Ti is set as a value based on a noise intensity estimated from a HAZE intensity detected by the regular reflection detection portion 104 and can be found using the following equation.

$$Ti=\sqrt{HAZE\,i}$$

At this time, if E (s)<1, the subject can be judged as a noise. If E (s)>1, the subject can be judged as a defect.

Figure 17:
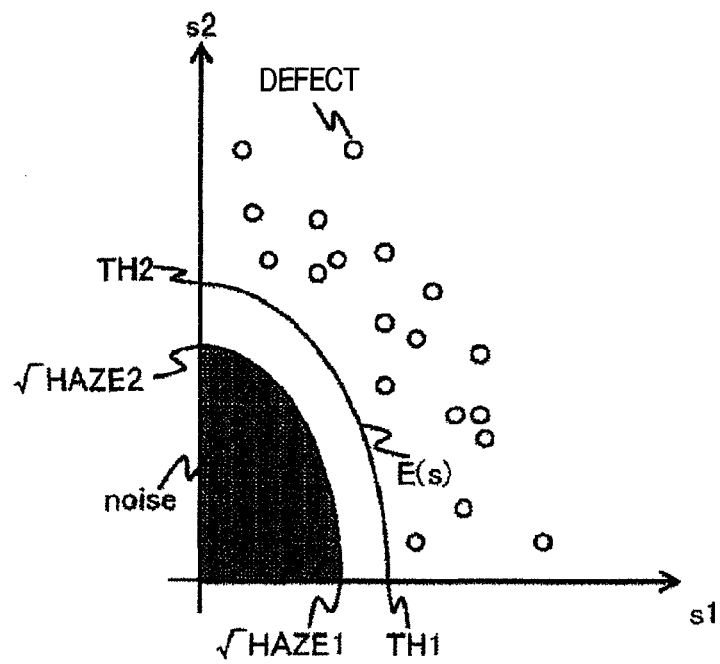
FIG. 17 is a conceptual diagram representing a threshold value based on an elliptic hypersphere.

FIG. 17 is a conceptual view representing a threshold value based on an elliptical hypersphere. FIG. 17 shows a decision boundary E when the feature space is taken to be two-dimensional. A defect decision using an nth-dimensional elliptical hypersphere threshold value produces the same results as yielded by a defect decision using an infinite number of sets of gain adjustment parameters in the above embodiment.

In the above embodiment, a boundary between noise and defect is determined based on an input detection signal. Here, a method of discriminating between noise and defects by collating input signals against preset decision criteria is described.

Figure 18:
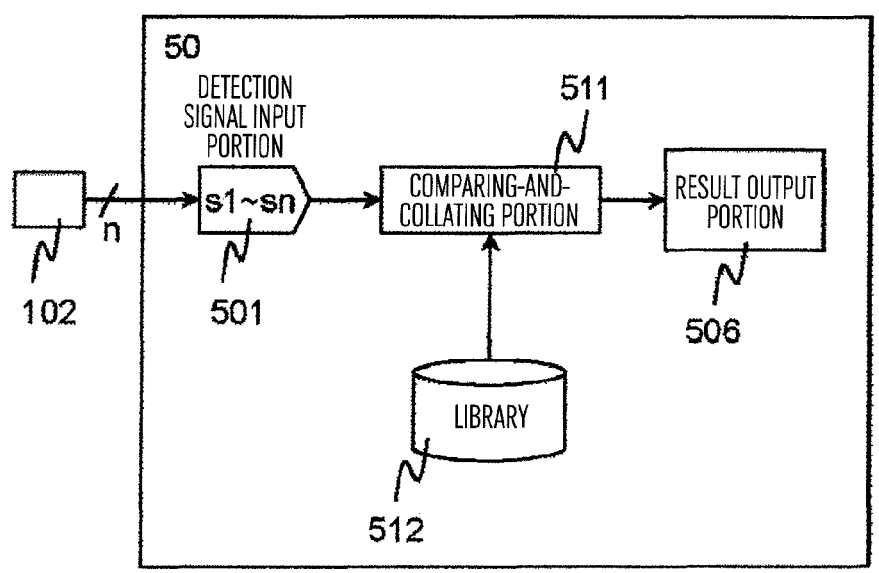
FIG. 18 is a block diagram showing the configuration of a signal processing portion.

FIG. 18 is a block diagram showing the configuration of a signal processing portion. Another form of the present embodiment is described by referring to FIG. 18.

It consists of the signal input portion 501 to which detection signals s1-sn obtained from the detectors 102 are applied, a comparing-and-collating portion 511 for determining noises and defects, the result output portion 506 for outputting results, and a library 512 for storing decision criteria that are input to the comparing-and-collating portion 511. The comparing-and-collating portion 511 compares and collates the input signals s1-sn with previously stored decision criteria in the nth-dimensional feature space and discriminates defects from noises.

One collation method consists of determining whether newly given points belong to noise or defect by the nearest neighbor rule under conditions where some points of noise and defect have been previously given by a user's instruction. Another method uses a decision criterion based on a neural network. A further method relies on a support vector machine. In addition, in the same way as in the above embodiment, input signals may directly use detection signal values indicative of scattering light intensities. Feature quantities extracted from detection signals may be employed.

Figure 19:
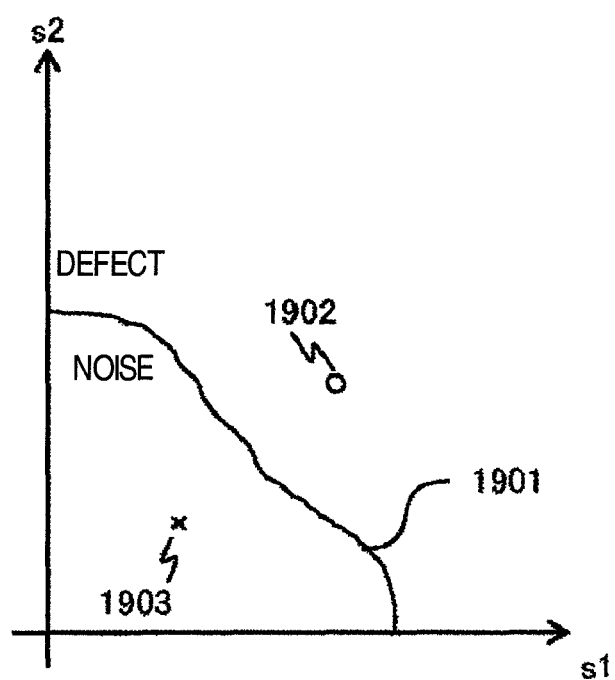
FIG. 19 is a conceptual view illustrating comparisons with a decision criterion.

FIG. 19 is a conceptual view showing comparisons with decision criteria. An example of feature space when an input signal is taken as two-dimensional is described by referring to FIG. 19. A boundary 1901 has been previously calculated and stored in a library. Input signals 1902 and 1903 are compared with the boundary and judged whether they are noises or defects. In this case, the input 1902 is judged as a defect, while the input 1903 is judged as a noise.

REFERENCE SIGNS LIST

1: wafer
2: laser light source
3: attenuator
4: polarizing element
5: illuminance distribution control device
6: condenser lens
7: beam expander
8: optical collection system
9: sensor
10: rotary stage
11: translational motion stage
13: polarizing filter
14: controller
15: light-blocking shutter
16: shutter controller
20: illumination spot
50: defect decision portion
51: feature quantity extraction portion
53: overall control portion
54: display portion
55: input portion
101: illumination portion
102*a*: detection portion
102*b*: detection portion
102*c*: detection portion
104: regular reflection detection portion
501: detection signal input portion
502: signal combining portion
503: signals
504: defect decision portion
505: result combining portion
506: result output portion
507: parameter storage library
508: gain adjustment parameter readout portion
509: threshold value setting portion
510: threshold readout portion
511: comparing-and-collating portion
512: decision criteria storage library

The invention claimed is:

1. A defect inspection device comprising:
an illumination optical portion configured to illuminate, with illuminating light, an object to be inspected;
a detecting optical portion illuminated by the illumination optical portion, and equipped with a plurality of detectors configured to detect components of scattered light scattered from the inspected object, each detector disposed in a different direction of azimuthal angle or in a different direction of angle of elevation with respect to a surface of the inspected object; and
a signal processing portion configured to perform defect determinations as to a plurality of signals, based on the scattered light components from the inspected object detected by the detectors, respectively, such that the defect determinations are performed in parallel, based on gain adjustments and threshold value decisions, and configured to extract defects based on results of the gain adjustments and defect determinations, wherein the signal processing portion includes:
a signal combining portion having a plurality of signal combining units, and configured to perform, in parallel, respective gain adjustments on a plurality of signals, the signals being based on the scattered light components received from the inspected object and detected by the plurality of detectors, wherein each signal combining unit is configured to perform gain adjustments respectively on the signals based on the scattered light components received from the inspected object and detected by the detectors, and wherein the signal combining units perform the gain adjustments using respectively different values of gain;

a defect decision portion having a plurality of defect decision units, and configured to perform, in parallel, defect determinations based on a preset threshold value, on the signals on which the gain adjustments have been made by the signal combining portion, wherein each defect decision unit is configured to perform defect determinations respectively on signals on which the gain adjustments have been made by the signal combining portion, and a result combining portion configured to combine results of the defect determinations made by the defect decision portion and configured to extract defects.

2. The defect inspection device according to claim 1, wherein the defect decision units make decisions as to respectively different species of defects.

3. The defect inspection device according to claim 1, wherein the gain values for the signal combining units are determined based on values set by a set of gain adjustment parameters.

4. The defect inspection device according to claim 1, wherein the threshold value for the defect decision units has been previously set by a threshold setting portion.

5. The defect inspection device according to claim 1, further comprising:

a display portion configured to display defects extracted by the signal processing portion.

6. The defect inspection device according to claim 1, wherein the signal combining units make gain adjustments for the signals, respectively, combine together the signals, on which the gain adjustments have been made, to calculate combined signals, and wherein combined signals calculated respectively by the signal combining units are applied to the defect decision units, respectively.

7. A defect inspection method comprising the steps of:

illuminating, with illuminating light, an object to be inspected;

detecting components of scattered light scattered from the inspected object, each detector disposed in a different direction of azimuthal angle or in a different direction of angle of elevation with respect to a surface of the inspected object by a plurality of detectors, respectively; and signal-processing, including the steps of:

making defect determinations in parallel on a plurality of signals based on the scattered light components, respectively, from the inspected object and detected by the detectors based on gain adjustments and threshold decisions, and extracting defects based on results of the gain adjustments and threshold decisions;

performing signal combining steps, including making respective gain adjustments, in parallel, on a plurality of signals that are based on the scattered light components detected by the detectors and received from the inspected object, wherein the gain adjustments are made in parallel using respectively different values of gain;

making defect determinations, based on a preset threshold value, in parallel on the plurality of signals on which the gain adjustments have been made by the signal combining steps; and performing a result combining step, including extracting defects by combining results of the defect determinations performed by the step of making defect determinations.

8. The defect inspection method according to claim 7, wherein during the defect decision step, decisions as to respectively different defect species are made.

9. The defect inspection method according to claim 7, wherein gain values used during the signal combining steps are determined based on values that have been set by the set of gain adjustment parameters.

10. The defect inspection method according to claim 7, wherein the threshold value used during the defect decision step has been previously determined by the threshold setting step.

11. The defect inspection method according to claim 7, further comprising the step of:

displaying defects extracted by the signal-processing step.

12. The defect inspection method according to claim 7, wherein during each of the signal combining steps, gain adjustments are made on the plurality of signals, and combined signals are calculated by combining the plurality of signals on which the gain adjustments have been made.

* * * * *